United States Patent
Zhnag et al.

(10) Patent No.: US 6,936,571 B2
(45) Date of Patent: Aug. 30, 2005

(54) FUNGICIDAL COMPOSITION CONTAINING PQDS

(76) Inventors: Hongyu Zhnag, Suite 102, Building 5, No. 12 Zhangzhou Road, Zibo City, Shandong Province (CN); Weizhong Liu, 5/F West, East Suite, Building 2, No. 533 Huanghesi Road, Binzhou City, Shandong Province (CN)

(*) Notice: Subject to any disclaimer, the term of this patent is extended or adjusted under 35 U.S.C. 154(b) by 0 days.

(21) Appl. No.: 10/277,076

(22) Filed: Oct. 21, 2002

(65) Prior Publication Data

US 2003/0216478 A1 Nov. 20, 2003

(30) Foreign Application Priority Data

May 10, 2002 (CN) .......................................... 2110386 A

(51) Int. Cl.[7] .............................................. A01N 35/00
(52) U.S. Cl. ........................ 504/348; 514/680; 424/405
(58) Field of Search .......................... 514/680; 504/348; 424/405

(56) References Cited

U.S. PATENT DOCUMENTS

2002/0031538 A1 * 3/2002 Scarmoutzos ............... 424/405

FOREIGN PATENT DOCUMENTS

CN          1183215      * 6/1998

* cited by examiner

*Primary Examiner*—Alton Pryor
(74) *Attorney, Agent, or Firm*—James B. Conte; Barnes & Thornburg

(57) ABSTRACT

The present invention provides an agricultural fungicidal composition containing active compounds selected from perylenequinonoid derivatives or salts thereof. The invention also relates the application of the composition against fungal plant infections.

8 Claims, No Drawings

FUNGICIDAL COMPOSITION CONTAINING PQDS

FIELD OF THE INVENTION

The present invention relates to an agricultural fungicidal composition, more particularly to a fungicidal composition containing an active compound selected from PQDs or a salt thereof, and the application of the composition against fungal plant infections.

BACKGROUND OF THE INVENTION

Traditional pesticides have disadvantage of tolerance problems when used a long time and somewhat harm to human. To overcome the drawbacks in the art, people have been developing new pesticides that are safer and more effective than those used in the art. It is the case that photosensitive compounds are developed as insecticides or fungicides.

Many photosensitive compounds exist in nature, but a great number of compounds that have photosensitive activity have been synthesized. Some of the compounds can generate active oxygen and a serial of free radicals under irradiation of light that harm organisms. Moreover, these compounds almost have no effect of toxicity to people. Therefore, people have paid much attention to the development of photosensitive compounds in the field of pesticides.

Chinese patents 96120600.4 and 96120599.7, of which the inventors of this application are co-inventors, disclose an insecticide composition comprising a natural perylenequinonoid, Hypocrellin A, and a method for preparing the same. However, perylenequinonoid derivatives (PQDs) as fungicides have not been disclosed in the art.

SUMMARY OF THE INVENTION

The inventors have found that perylenequinonoid derivatives (PQDs) with a chemical structure of 4-hydroxyl-3,10-perylenequinonoind are of photosensitive activity and can be used to control harmful fungi.

Therefore, one object of the invention is to provide a fungicidal composition comprising a fungicidally effective amount of a compound selected from perylenequinonoid derivatives (PQDs) or a salt thereof and an agriculturally acceptable carrier.

Perylenequinonoid derivatives used as fungicides in the invention have a common formula (I):

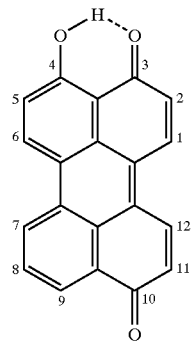

(I)

Another object of the invention is to provide a method for controlling harmful fungi, which comprises treating the harmful fungi, their habitat, or plants, seeds, soils, areas, materials or spaces to be kept free from the fungi with an effective amount of a compound selected from PQDs or a salt thereof.

In the invention, the perylenequinonoid derivatives may be either those that have been synthesized and disclosed publicly or natural products that are extracted from species containing PQDs. The term PQD(s) as used in the claims is limited to a perylenequinonoid derivative having the general formula (I) as set forth above.

Yet another object of the invention is to provide a method for preparing an extract of PQD-containing species which comprises:

(a) cutting the species into small pieces, if necessary;
(b) contacting said species or pieces with an organic solvent at room temperature for from 0 hours to 72 hours, and then heating to reflux from 20 minutes to 120 minutes to form a solution and debris;
(c) removing said debris from said solution; and
(d) evaporating said solution to form a paste.

Still another object of the invention is to provide a method for protecting plants against fungal infections, comprising the steps of:

(a) preparing an extract of PQD-containing species by
(i) contacting small pieces of the species with an organic solvent at room temperature from 0 hours to 72 hours, and then heating to reflux from 20 minutes to 120 minutes to form a solution and debris;
(ii) removing said debris from said solution;
(iii) evaporating said solution to form a paste; and
(iv) mixing said paste with a carrier to form a fungicidal composition, and
(b) applying a fungicidally effective amount of the fungicidal composition to the plants for protecting against fungal infections.

DETAILED DESCRIPTION OF THE INVENTION

The perylenequinonoid derivatives used in the fungicidal composition include both natural products and synthesized products that have been disclosed publicly. The natural products are preferable. The natural PQDs include Hypocrellin A, Hypocrellin B, Elsinochrome A, Elsinochrome B, Elsinochrome C, Phleichrome, Cercosporin, Cladochrome A, Cladochrome B, Cladochrome C, Cladochrome D, Aphins A, Aphins B, Hypericin, Stentorin, Hypomycin A and Hypomycin B.

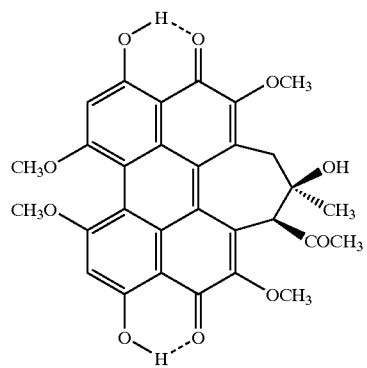

Hypocrellin A

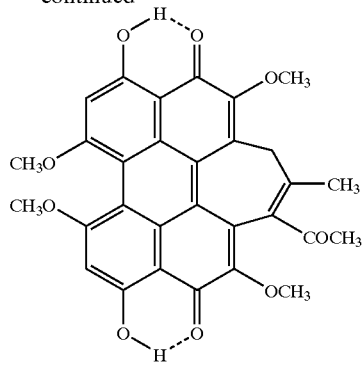

Hypocrellin B

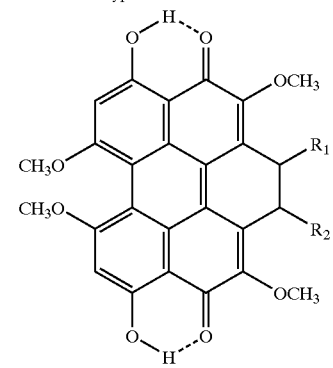

Elsinochrome

Elsinochrome A: R₁ = R₂ = COMe
Elsinochrome B: R₁ = COMe, R₂ = CH(OH)Me
Elsinochrome C: R₁ = R₂ = CH(OH)Me

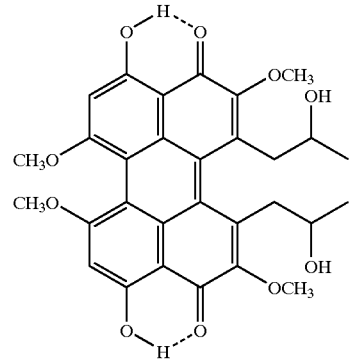

Phleichrome

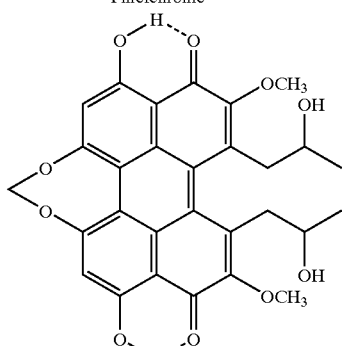

Cercosporin

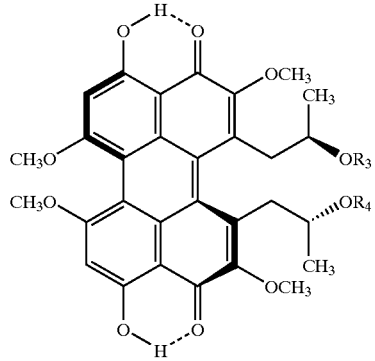

Cladochrome

Cladochrome A: R₃ = R₄ = H
Cladochrome B: R₃ = R₄ = COCH₂CH(OH)Me
Cladochrome C: R₃ = COCH₂CH(OH)Me; R₄ = COPh
Cladochrome D: R₃ = COPh; R₄ = CO-p-PhOH

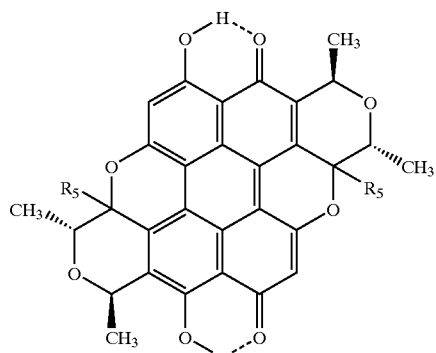

Aphins

Aphins A: R₅ = H
Aphins B: R₅ = OH

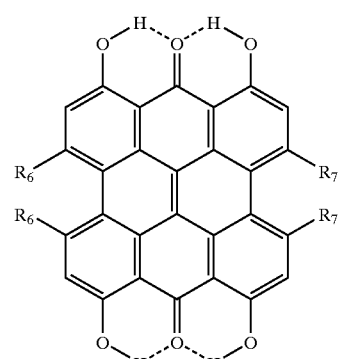

Hypericin: R₆ = OH; R₇ = CH₃
Stentorin: R₆ = R₇ = OH

-continued

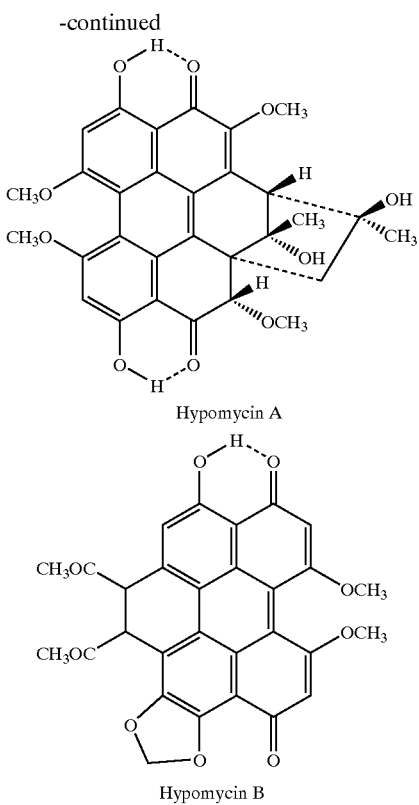

Hypomycin A

Hypomycin B

The term "active component" used in the invention" denotes a compound of formula (I), or its inorganic salt, or a mixture thereof. PQDs are preferably used in the invention.

The active component in the composition according to the invention is employed in a purity of from 0.1% to 100%, depending on the source of PQDs used. For example, when a synthesized PQD is used, it can be used in a purity of 100%.

The term "effective amount" means an amount of the active component used can effectively control harmful fungi. Compositions according to the invention generally contain between 0.1% and 99.9% by weight of active components, preferably between 0.5% and 95% by weight, more preferably between 5% and 80% by weight, and most preferably between 10% and 75% by weight.

The term "carrier" used in the invention denotes a natural or synthetic, organic or inorganic material with which the active component is combined to facilitate its application on the plant, on seeds or on the ground. The carrier is thus generally inert or at least inert to the active component and must be agriculturally acceptable. The carrier can be solid such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, resins, waxes, fertilizers such as ammonium sulfate, ammonium phosphate, ammonium nitrate and ureas, products of vegetable origin such as cereal meal, tree bark meal, wood meal and nutshell meal, cellulose powders and the like, or liquid such as water, alcohols, ketones, petroleum fractions, aromatic or paraffinic hydrocarbons, chlorinated hydrocarbons, liquefied gases and the like.

The carrier used in the composition of the invention can further comprise a surface active agent (surfactant), which can be an emulsifying, dispersing or wetting agent of ionic or nonionic type. Suitable surface-active agents may be non-ionic, anionic or cationic with good dispersing, emulgating and wetting properties depending on the nature of the active component to be formulated.

Suitable surface active agents includes, but not limited to, fatty sulphonates, fatty sulphates or alkyl aryl sulphonates. The fatty sulphates or fatty sulphonates are normally used as alkali, earth alkali or optionally substituted ammonium salts and have an alkyl moiety of 8 to 22 carbon atoms, whereby alkyl also means the alkyl moiety of acyl residues, such as the sodium or calcium salt of lignin sulphonic acid, of sulphuric acid dodecylate or of a mixture of fatty alcohols prepared from natural fatty acids. Alkyl aryl sulphonates are, for example, the sodium, calcium or triethyl ammonium salts of dodecyl benzene sulphonic acid, dibutyl naphthalene sulphonic acid or of a condensate of naphthalene sulphonic acid and formaldehyde. Furthermore, phosphates, such as the salts of the phosphoric acid ester of a p-nonylphenol-(4-14)-ethylene oxide adduct or phospholipids, may be used in the invention.

Non-ionic surface active agents are preferably polyglycol ether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols. Other suitable non-ionic surface active agents are the water-soluble, 20 to 200 ethylene glycol ether groups containing polyadducts of ethylene oxide and polypropylene glycol, ethylene diamino polypropylene glycol and alkyl polypropylene glycol with 1 to 10 carbon atoms in the alkyl moiety, the substances normally contain 1 to 5 ethylene glycol units per propylene glycol unit. Examples of non-ionic surface active agents are nonylphenol polyethoxy ethanols, castor oil polyglycol ether, polyadducts of ethylene oxide and polypropylene, tributyl phenoxy polyethoxy ethanol, polyethylene glycol, octyl phenoxy polyethoxy ethanol, Tween serials such as polyoxyethylene sorbitan monolaurate, polyoxyethylene sorbitan monopalmitate and polyoxyethylene sorbitan monooleate. In addition, fatty acid esters of polyoxy ethylene sorbitan, such as polyoxy ethylene sorbitan trioleate may be used.

When the component in the composition comes from the natural product, it is preferably prepared by extraction from PQD-containing species. In general, Hypocrellin A and Hypocrellin B come from *Hypocrella bambusae, Sharaia bambusiola P. Henn* or an artificially incubated *Hypomyces* (Fr.) *Tul.*sp.; Elsinochrome A, Elsinochrome B and Elsinochrome C are from Elsinoe or *Hypomyces* (Fr.) *Tul.*sp.; Phleichrome comes from *Cladosporium phlei;* Cercosporin is from *Crecosporium kikuchii;* Cladochrome A, Cladochrome B and Cladochrome C and Cladochrome D are from *Cladosporium cucumerinum;* Aphins A and Aphins B come from Aphids; Hypericin is from *Hypericum perforatum* L, *Hypericum perzoratum* and *H. triquetrifolium Turra;* ; Stentorin is from *Stenor coeruleus;* and Hypomycin A and Hypomycin B come from *Hypomyces* (Fr.) *Tul.*sp.

The organic solvent used for extraction in the invention is taken from the group which includes, but is not limited to, $C_{1-4}$ alkyl alcohol, n-hexane, chloroform, ethylacetate, diethylether or their mixtures thereof. $C_{1-4}$ alkyl alcohols are preferable. Ethanol is most preferable.

Crude materials used for extraction of the active component PQD in the invention may include those species containing PQDs such as natural fungi, plants and animals, or artificially cultured mycelium, or artificially cultured plant and animal cells. When the PQD-containing species for extraction are plants, the plants are preferably cut into small pieces.

The extraction can be carried out by using a ratio of volume of organic solvents to weight of the material of about one liter of organic solvent to from about 50 to about 500 g of materials. The materials can be dipped with the solvent for from 0 to 72 hours. Then the resultant is heated to reflux for from 20 minutes to 120 minutes. It is appreciated that the shorter the dipping of the material, the longer the reflux is carried out. Preferably, the material is dipped for from 12 hours to 24 hours, and the reflux is taken for from 45 minutes to 90 minutes.

After extraction, the pieces are discarded, the resultant extract is filtered to remove debris from the solution and the solvent is evaporated under ambient pressure, or under reduced pressure. The extract thus obtained is a brown-yellow or brown-black paste. This paste is then dissolved in an organic solvent taken from the group which includes, but is not limited to, $C_{1-4}$ alkyl alcohol, n-hexane, chloroform, acetone, ethylacetate, diethylether or their mixtures thereof. Alternatively, the paste can be dissolved in water with the aid of an additive, such as an appropriate emulsifier or emulsifiers. The resultant solution may be formed to be various formulations upon requirements.

The composition can be formulated as powders, wettable powders, emulsion concentrates, dusts, granules, solutions and other formulations.

Powders and dusts can be prepared by mixing or jointly grinding the active compound or compounds with a solid carrier. Granules (e.g. coated granules, impregnated granules or homogeneous granules) are usually prepared by binding the active component to a solid carrier. Solutions are used prepared by dissolving the active component in a liquid carrier, with a surface active agent if necessary.

In the method for protecting plants against fungal infections according to this invention, the preferred concentration of the paste in a carrier used in the method for protecting plants against fungal infections ranges from about 0.1 to about 99.9 percent by weight of paste per volume of the carrier. Solutions containing the PQDs extract are sprayed onto the leaf surfaces of various crop plants for the control of fungal plant infections. Actual amount of the active component used is known for those skilled in the art according to fungi to be treated, plants to which the composition is to be applied and other factors.

The method of the invention is particularly suitable for use against fungi of the Leukoderma, Oomycetes, Ascomycetes and *Fungi imperfecti* classes including but not limited to *Cladosporium cucumerinum, Phytophthora parasitica, Botrytis cinerea, Pseudoperonospora cubensis, Sphaerotheca fuliginea, Fusarium oxysporum, Erwinia aroideac, Glomerella cingulata, Mycosphaerella pinoides, Pellicularia filamentosa, Peronospora brassicae, Pseudomonas maculicola, Pseudomonas solanacearum, Puccinia graminis, Sclerotinia sclerotiorum, Turnip mosaic* virus, *Xanthomonas phaseoli, Armillariella mellea, Collectotrichum lagenarium, Corticium rolfsii,* and *Erysiphe graminis* in crops, fruits and vegetables including but not limited to grapevines, cucumber, tomato, corn, wheat, barley, soybean, broomcorn, and potato.

The invention is illustrated by the following examples, which describe the preparation of composition containing PQDs and use of PQDs extracts against fungal infections in plants.

EXAMPLE 1

Preparation of PQDs-containing Extract

Preparation A

To 1 kg of *Hyporella bambusae* coming from Yunnan Province, China was added 10L of 95% alcohol. After kept 12 h at ambient temperature, resultant solution was heated to rereflux for 2 hours. The debris was removed by filtration. The solvent was then evaporated under ambient pressure to obtain a paste, 99.5 g. The paste contained 39.2 g Hypocrellin A and 10.6 g Hypocrellin B by HPLC.

Preparation B 1 kg of dried leaves and stems of *Hypericum perforatum* L (or *hypericum perzoratum, H. triquetrifolium Turra*) were first grounded into powder of 60–100 mesh, then were dipped into 10 liters of methanol at 45°–50° C. for 48 h. The solution was heated to reflux for 20 minutes. After filtered to remove debris, the solvent was evaporated at reduced pressure to obtain a paste, 20.5 g. The paste contained a Hypericin 4.9 g by HPLC.

| | |
|---|---|
| Example 2 | |
| Emulsion Concentrates | |
| Hypericin | 2 g |
| Tween-20 | 30 g |
| Ethanol | 68 g |
| Example 3 | |
| Suspension Concentrates | |
| Phleichrome | 5 g |
| Castor oil polyglycol ether | 20 g |
| Water | 75 g |
| Example 4 | |
| Wettable Powders | |
| PQD extract prepared as Preparation B | 0.5 g |
| OP-15 | 20 g |
| Clay | 79.5 |
| Example 5 | |
| Dusts | |
| Hypericin | 1 g |
| Kaolin | 99 g |
| Example 6 | |
| Granulates | |
| Elsinochrome A | 0.5 g |
| Talc | 99.5 |

EXAMPLE 7

Solution 0.05 kg of paste prepared according to the method of Preparation A was dissolved in 1000 ml of ethanol to obtain a solution. To the solution were added 3 kg of Tween-40 and 6 liters of water to a fungicide composition of the invention.

EXAMPLE 8

Solution

To 100 g of phleichrome, prepared by the method of C. A. Broka, Tetrahedron Letter, 1991, 32:859–862, was added 2000 ml of methanol. The resultant was slightly heated until phleichrome was completely dissolved. 4 kg of Tween-20 and 14 liters of water were added to the resultant solution, to obtain a fungicide solution of the invention.

EXAMPLE 9

Bioactivity of the Composition According to the Invention

Test 1 Effect of the Composition of the Invention against Gray Mold of Cucumber Materials:

0.33% of Hypocrellin A and Hypocrellin B solution prepared as Example 7

75% wettable powder of chlorothalonil commercially available produced by Yunnan Chemical Factory 50% wettable powder of iprodione commercially available produced by Rone Planck Fungi to Be Tested:

*Botrytis cinerea* cultured with PDA media

Method of Test:

5 PQD solutions (1 ml) with different concentrations (50 times higher than that to be tested) were respectively mixed with 49 ml of PDA media. They were then poured into 4 sterile cultural dishes. After coagulation, *Botris cinerea* of cucumber (fungi paste with a diameter of 0.6 cm) was inoculated and incubated at 25° C. for 72 h in an incubating chamber with light. The diameter of the colony was determined and inhibitory rate was determined. The results were listed in table 1.

TABLE 1

| Items | Concentrations (mg/L) | Diameter of Colony | Inhibitory Rate (%) | $IC_{50}$ (mg/L) |
|---|---|---|---|---|
| 0.33% PQD Solution | 0 | 3.20 | — | 4.2038 |
| | 1.6 | 2.15 | 32.1 | |
| | 3.2 | 1.80 | 43.75 | |
| | 6.4 | 1.18 | 63.13 | |
| | 12.8 | 0.98 | 69.38 | |
| | 25.6 | 0.88 | 72.50 | |
| 10% Alcohol | 0 | 3.20 | — | |
| | 100 | 3.00 | 6.25 | |
| | 200 | 3.15 | 1.56 | |
| | 400 | 3.05 | 4.69 | |
| | 800 | 3.10 | 3.13 | |
| | 1600 | 3.18 | 0.63 | |
| 75% wettable powder of Chlorothalonil | 0 | 3.20 | — | 5.0195 |
| | 4 | 2.30 | 28.13 | |
| | 8 | 2.08 | 35.00 | |
| | 16 | 0.96 | 70.00 | |
| | 32 | 0.75 | 76.56 | |
| | 64 | 0.23 | 92.81 | |
| 50% wettable powder of Iprodione | 0 | 3.20 | — | 0.3925 |
| | 0.1 | 5.38 | 18.75 | |
| | 0.2 | 1.83 | 25.63 | |
| | 0.4 | 1.73 | 45.94 | |
| | 0.8 | 1.10 | 65.65 | |
| | 1.6 | 0.30 | 90.63 | |

The results showed that the effect of 0.33% PQD aqueous solution on controlling *Botris cinerea* of cucumber was better than that of 75% wettable powder of chlorothalonil.

Test 2 Effect of the Composition of the Invention against Early Blight of Tomato Materials:

0.33% of Elsinochrome A solution in water

75% wettable powder of chlorothalonil commercially available produced by Yunnan Chemical Factory Fungi to Be Tested:

*Alternaria solani* of tomato cultured with PDA media

Method of Test:

5 PQD solutions (1 ml) with different concentrations were respectively mixed with 49 ml of PDA media. They were then poured into 4 sterile cultural dishes. After coagulation, *Alternaria solani* of tomato (fungi paste with a diameter of 0.6 cm) was inoculated and incubated at 25° C. for 72 h in an incubating chamber with light. The diameter of colonies was determined and the inhibitory rate was determined. The results were listed in Table 2.

TABLE 2

| Items | Concentrations (mg/L) | Diameter of Colony | Inhibitory Rate (%) | $LC_{50}$ (mg/L) |
|---|---|---|---|---|
| 0.33% PQD Solution | 0 | 2.90 | — | 0.3310 |
| | 0.065 | 2.23 | 23.10 | |
| | 0.13 | 2.13 | 26.55 | |
| | 0.26 | 1.78 | 38.62 | |
| | 0.52 | 1.15 | 60.34 | |
| | 1.04 | 0.68 | 76.55 | |
| 10% Alcohol | 0 | 2.90 | — | |
| | 125 | 2.90 | 0 | |
| | 250 | 2.68 | 7.59 | |
| | 500 | 2.73 | 5.86 | |
| | 1000 | 2.68 | 7.59 | |
| | 2000 | 2.75 | 5.17 | |
| 75% wettable powder of Chlorothalonil | 0 | 2.90 | — | 23.1163 |
| | 4 | 2.28 | 21.38 | |
| | 8 | 1.85 | 36.21 | |
| | 16 | 1.65 | 43.10 | |
| | 32 | 1.38 | 52.41 | |
| | 64 | 0.92 | 68.28 | |

Table 2 showed that the effect of 0.33% PQD aqueous solution on controlling *Alternaria solani* of tomato was much better than that of 75% wettable powder of chlorothalonil.

Test 3 Effect of the Composition of the Invention against *Botryosphaeria beregeriana* of Apple Materials:

0.55% of Hypericin solution prepared as Example 3

50% wettable powder of carbendazol commercially available produced by Xinyi Pesticides Co., Ltd, China 70% wettable powder of thiophate methyl commercially available produced by Xinyi Pesticides Co., Ltd, China Fungi to Be Tested:

*Botryosphaeria beregeriana* of apple cultured with PDA media

Method of Test:

5 PQD solutions (1 ml) with different concentrations were respectively mixed with 49 ml of PDA media. They were then poured into 4 sterile cultural dishes. After coagulation, *Botryosphaeria beregeriana* of apple (fungi paste with a diameter of 6 mm) was inoculated and incubated at 25° C. for 72 h in an incubating chamber (L:D=16:8). The diameter of colonies was determined and the inhibitory rate was determined. The results were listed in table 3.

TABLE 3

| Items | Concentrations (mg/L) | Diameter of Colony | Inhibitory Rate (%) | Virulence |
|---|---|---|---|---|
| 0.55% PQD Solution | 0 | 2.40 | — | 27.09 |
| | 0.7 | 1.43 | 40.42 | |
| | 1.4 | 1.25 | 47.92 | |
| | 2.8 | 0.87 | 63.75 | |
| | 5.6 | 0.70 | 70.83 | |
| | 11.2 | 0.61 | 74.58 | |
| 50% wettable powder of Carbendazol | 0 | 2.40 | — | 867.4 |
| | 0.0125 | 2.14 | 10.83 | |
| | 0.025 | 1.65 | 31.25 | |
| | 0.05 | 1.07 | 55.42 | |
| | 0.1 | 0.33 | 86.25 | |
| | 0.2 | 0.23 | 90.42 | |
| 70% wettable powder of Thiophanate methyl | 0 | 2.40 | — | 100 |
| | 0.1 | 2.30 | 4.17 | |
| | 0.2 | 1.77 | 26.25 | |
| | 0.4 | 0.63 | 73.75 | |
| | 0.8 | 0.41 | 89.92 | |
| | 1.6 | 0.25 | 89.58 | |

The results showed that 0.55% PQD aqueous solution had effects on controlling *Botris cinerea* of cucumber, and virulence thereof was much lower than carbendazol 50% wp and thiophanate methyl 70% wp.

The above description and examples are only used to illustrate the invention. It is appreciated that any modifications or variations to the invention without departing from the spirit of the invention belong to the scope of the invention.

What is claimed is:

1. A method for controlling harmful fungi, which comprises treating a plant with an effective amount of a compound selected from perylenequinonoid derivatives (PQDs) or an acceptable salt thereof, excluding hypericin, wherein said effective amount of compound is between 5% to 80% by weight of a composition containing said compound, and wherein said effective amount is fungicidally effective, and said effective amount is applied to said plant for protecting against fungal infection.

2. A method for controlling harmful fungi, which comprises treating a plant with an effective amount of a compound selected from PQDs or an acceptable salt thereof, by applying a fungicidally effective amount of a PQD extract to said plant for protecting against fungal infection, wherein said plant is selected from the group consisting of grapevines, cucumber, tomato, corn, wheat, barley, soybean, broomcorn, and potato.

3. A method for controlling harmful fungi, which comprises treating a plant with an effective amount of a compound selected from PQDs or an acceptable salt thereof, by applying a fungicidally effective amount of a PQD extract to said plant for protecting against fungal infection, wherein said fungi is caused by phytopathogenic fungi of a class selected from the group consisting of Leukoderma, Oomycetes, Ascomycetes and Fungi imperfecti.

4. A method for controlling harmful fungi, which comprises treating a plant with an effective amount of a compound selected from PQDs or an acceptable salt thereof, by applying a fungicidally effective amount of a PQD extract to said plant for protecting against fungal infection, wherein said fungal infection is caused by a fungus selected from the group consisting of *Cladosporium cucumeripum, Phytophthora parasitica, Botrytis cinerea, Pseudoperonospora cubensis, Sphaerotheca fuliginea, Fusarium oxysporum, Erwinia aroideae, Glomerella cingulata, Mycosphaerella pinoides, Pelliculana filamentosa, Peronospora brassicae, Pseudomonas maculicola, Pseudomonas solanacearum, Puccinia graminis, Sclerotinia sclerotiorum, Turnip mosaic virus, Xanthomonas phaseoli, Armillariella mellea, Collectotrichum lagenarium, Corticium rolfsii,* and *Erysiphe graminis.*

5. A method for controlling harmful fungi, which comprises treating a plant with an effective amount of a compound selected from PQDs or an acceptable salt thereof, by applying a fungicidally effective amount of a PQD extract to said plant for protecting against fungal infection, wherein the compound is selected from a group of compounds consisting of Hypocrellin, Elsinochrome, Phleichrome, Cercosporin, Cladochrome, Aphins, Stentorin, Hypomycin, and mixtures thereof.

6. The method of claim 5, wherein the compound is Hypocrellin.

7. A method for controlling harmful fungi, which comprises treating a plant with an effective amount of a compound selected from PQDs or an acceptable salt thereof, by applying a fungicidally effective amount of a PQD extract to said plant for protecting against fungal infection, wherein the PQD-containing species is *Hypocrella Bambufae.*

8. A method for protecting plants against fungal infections, comprising:

the steps of
(a) preparing an extract of PQD-containing species by
(i) contact the species with an organic solvent at room temperature from 0 hours to 72 hours, and then heating to reflux from 20 minutes to 120 minutes to form a solution and debris;
(ii) removing said debris from said solution;
(iii) evaporating said solution to form a paste; and
(iv) dissolving said paste in a carrier to form a fungicidal composition, and
(b) applying a fungicidally effective amount of said fungicidal composition to a plant for protecting against fungal infection.

* * * * *